United States Patent [19]

Crooks et al.

[11] Patent Number: 5,044,380
[45] Date of Patent: Sep. 3, 1991

[54] APPARATUS AND METHOD FOR STUDYING SMOKE COMPONENTS

[75] Inventors: Evon L. Crooks, Winston-Salem; Jerry S. Simmons, Garner, both of N.C.

[73] Assignee: R. J. Reynolds Tobacco COmpany, Winston-Salem, N.C.

[21] Appl. No.: 478,710

[22] Filed: Feb. 8, 1990

[51] Int. Cl.$^5$ .............................................. A24C 5/60
[52] U.S. Cl. ................................. 131/329; 73/863.01; 73/863.22; 73/863.44
[58] Field of Search ............. 131/329; 73/863, 863.01, 73/863.03, 863.21, 863.22, 863.23, 863.44

[56] References Cited

U.S. PATENT DOCUMENTS

| | | |
|---|---|---|
| 3,433,054 | 3/1969 | Mutter . |
| 3,460,374 | 8/1969 | Parks . |
| 4,140,003 | 2/1979 | Pillsbury et al. . |
| 4,204,550 | 5/1980 | Newman et al. . |
| 4,836,223 | 6/1989 | Burghart et al. . |

OTHER PUBLICATIONS

P. Ceschini et al., "Evolution of the Gas-Vapour Phase and the Total Particulate Matter of Cigarette Smoke in a Single Puff", pp. 378–381, Beitraege zur Tabakforschung, vol. 6 (1976).

B. Ingebrethsen, "Evolution of the Particular Size Distribution of Mainstream Cigarette Smoke During a Puff", pp. 423–433, Aerosol Science and Technology (1986).

Primary Examiner—V. Millin

[57] ABSTRACT

An apparatus for collecting samples of smoke components from predetermined segments of drawn smoke during a predetermined time interval is disclosed. The apparatus includes a smoking machine for drawing successive individual puffs of smoke from a cigarette and for providing a predetermined path of travel for drawn smoke. The particulate matter of the drawn smoke is collected on a filter pad positioned on a movable stage for providing relative movement between the filter pad and the path of travel of the drawn smoke. Advantageously, the filter pad is moved transversely relative to the path of travel of the drawn smoke. A method for collecting samples of smoke components of drawn smoke is also provided.

11 Claims, 2 Drawing Sheets

APPARATUS AND METHOD FOR STUDYING SMOKE COMPONENTS

FIELD AND BACKGROUND OF THE INVENTION

The present invention relates to an apparatus and method for collecting samples of smoke components from predetermined segments of a smoke stream during a predetermined time interval.

Considerable attention has been given to the study of specific compounds of the mainstream smoke of smoking articles. Various techniques have been suggested for measuring the yields of the mainstream smoke compounds. Among these techniques are assaying methods such as gas chromatography, radioisotope labelling and the like. These techniques, however, provide information about the specific overall composition of the smoke rather than the concentration of a particular component during a predetermined time interval within each individual puff.

A technique utilizing a smoking machine which separates the particulates from sequential puffs of a cigarette has been proposed in U.S. Pat. No. 3,433,054 to Mutter. The smoking machine utilizes a series of cigarettes mounted on a primary wheel and a series of filters mounted on a secondary wheel. The two wheels are rotated in a manner so that the first puff from each individual cigarette is drawn through a first filter unit, a second puff is taken from the individual cigarette and drawn through a second filter unit, and so on, thereby providing for collection of drawn smoke components from each puff. U.S. Pat. No. 3,433,054 to Mutter does not suggest collecting components at specified times during an individual puff.

A technique for measuring smoke components at specified times during a puff has been suggested by Ceschini et al in *Beitr. Tabakforsch* Volume 6, page 378–381 (1976). The concentration of mainstream smoke components is studied by testing the various thirds composition of a single puff, rather than testing the composition of the entire continuous puff.

U.S. Pat. No. 4,204,550 to Newman et al proposes an apparatus for collecting smoke components within a puff. The apparatus collects the particulates from each puff as an arcuate band on a filter mounted so as to rotate at a controlled azimuthal speed. However, it is expected that the cyclical path of travel results in a radially nonuniform distribution inasmuch as the inner portion of the arcuate band may have a heavier deposition of particulates than the outer portion of the arcuate band. Analysis of the collected components can be complicated by the need to take account of the preferential non-uniform distribution effect.

It would be desirable to provide an apparatus and method for collecting smoke components from predetermined segments of the individual puffs during a predetermined time interval.

SUMMARY OF THE INVENTION

The present invention relates to an improved apparatus and methods for collecting components of mainstream smoke of a smoking article, such as a cigarette.

In one aspect, the invention relates to an apparatus for collecting components of mainstream smoke of a smoking article. The apparatus includes a smoking machine for drawing successive individual puffs of smoke from the smoking article and for providing a predetermined path of travel for drawn smoke. The apparatus also includes a collection assembly for collecting a discrete sample quantity (i.e. amount) of smoke components from the drawn smoke during a predetermined time interval within each individual puff. The collection assembly includes (i) a filter pad positioned within (e.g. perpendicular to) the predetermined path of the drawn smoke for collecting smoke components therefrom, and (ii) a movable stage for providing relative movement of the filter pad across the path of travel of the drawn smoke, for the purpose of collecting discrete sample amounts of uniform distribution on different (e.g. sequential) portions or segments of the filter pad. The drawn smoke components are collected during a predetermined time interval within each individual puff.

In another aspect, the invention relates to an apparatus having a smoking machine and collection assembly which includes (i) a filter pad positioned within (e.g. perpendicular to) the predetermined path of the drawn smoke for collecting smoke components therefrom, and (ii) a movable stage for providing relative transverse movement of the filter pad across the path of travel of the drawn smoke, for the purposes of collecting discrete sample amounts on different (e.g. sequential) portions or segments of the filter pad. The drawn smoke compounds are collected during a predetermined time interval within each individual puff. Advantageously, the stage causes transverse movement of the filter pad relative to the path of travel of the drawn smoke. Additionally, in a preferred embodiment, the collection assembly includes a mount for securing the filter pad and for allowing removal thereof after each successive individual puff.

In another aspect, the invention relates to a method for collecting components of mainstream smoke of a smoking article comprising the steps of drawing an individual puff of smoke from the smoking article along a predetermined path of travel and transversely moving a filter pad relative to the path of travel of the drawn smoke to collect discrete sample amounts of smoke components from the drawn smoke. The samples are collected on different (e.g. sequential) portions or segments of the filter at predetermined time intervals. Advantageously, the method may include removing the filter, inserting a new filter and repeating the first two steps until the smoking article is substantially completely smoked.

BRIEF DESCRIPTION OF THE DRAWINGS

In the drawings which form a part of the disclosure.

DESCRIPTION OF THE PREFERRED EMBODIMENT.

Figure 1:
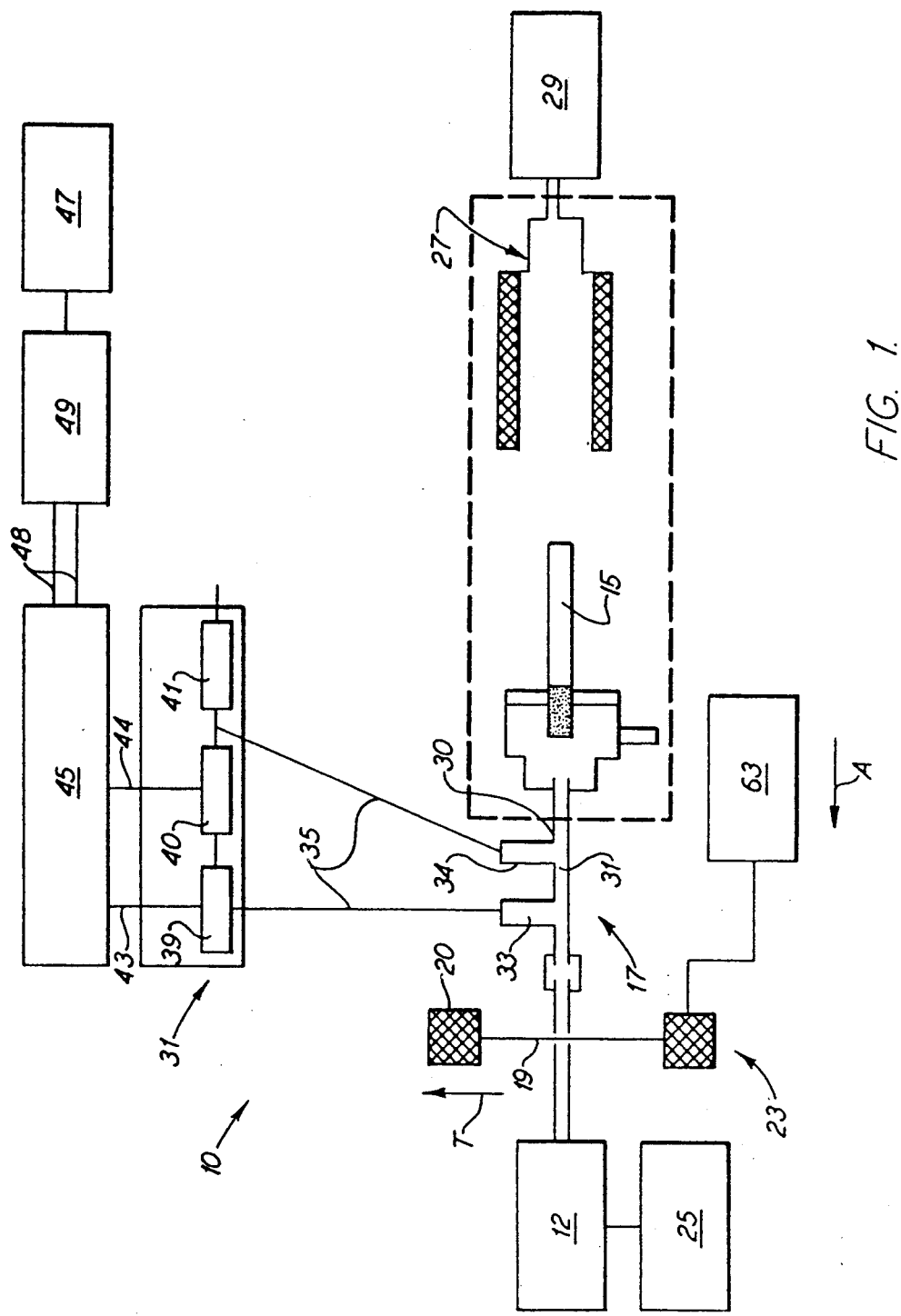
FIG. 1 is a schematic view of a preferred apparatus of the present invention.

Referring to FIG. 1, a preferred apparatus 10 includes a piston-type smoking machine 12 or other means for drawing successive individual puffs of smoke from a cigarette 15 and for providing a predetermined path of travel for drawn smoke in the direction of arrow A. The air flow rate in the direction of the path of travel is monitored by a flow sensor 17. The smoke components of the drawn smoke are collected on a Cambridge filter pad 19, or other suitable filter means, which is mounted on mount 20. The filter pad 19 and mount 20 are positioned on a movable stage 23 or other means for providing relative movement between the filter pad 20 and the path of travel of the drawn smoke in the direction of arrow A. The mount 20 allows removal of the filter pad 19 therefrom after each successive individual puff and reinsertion of the filter pad 19 therein before the next individual puff.

A preferred piston-type smoking machine 12 is the Filamatic® smoking machine manufactured by National Instrument Company of Baltimore, Md. Such a smoking machine 12 utilizes a piston to displace a known volume of air for a predetermined time interval at a predetermined frequency as controlled by a timer 25. Generally, the smoking machine 12 is set to the standard smoking conditions of puff volume, puff duration and puff frequency established by the U.S. Federal Trade Commission (FTC). The FTC standard smoking conditions consist of a 35 cc puff of 2 second duration taken every 60 seconds. A typical cigarette yields about 5 to 12 puffs.

The smoking machine 12 is connected to an enclosure 27 which, by vacuum action, provides a means for initiating a puff of the cigarette 15. A typical enclosure 27 is a glass tube, 15 cm in length and 2 cm in diameter, and is of such a size to enclose the length of the cigarette 15. The enclosure 27 is connected to a pneumatic actuator (not shown), such as Model AP3/4x6 manufactured by Tom Thumb of Ft. Wayne, Ind., and moves the enclosure 27 to enclose the cigarette 15. The movement of the pneumatic activator is controlled by a valve (not shown) such as a two-way solenoid valve available as Model F53 manufactured by Skinner Electric Valve Co. of New Britain, Conn. The valve is connected to a pressure source (not shown) and is activated by timer 25. A typical pressure source is one that maintains a pressure of about 15 psi.

To initiate a puff, the timer 25 activates closure of the valve by releasing pressure on the pneumatic activator. The closure of the valve causes the enclosure 27 to close around or surround the cigarette 15 by moving the enclosure 27 in direction of arrow A. When the enclosure is in its closed position, namely, enclosing the cigarette, a relay (not shown) is triggered, initiating a puff. During the smolder period between puffs, the enclosure 27 is retracted from around the cigarette and remains stationary away from the cigarette 15 until activated again by the timer 25 to again enclose the cigarette. The movement of the enclosure 27 provides a means for initiating data acquisition of flow rates through the cigarette during the puff period.

The smoking machine 12 is also connected to the flow sensor 17 which measures the flow rate of the drawn smoke. A flow meter 29, such as a Model 209-SE flow meter manufactured by Custom Electronics System, Inc. of Winston-Salem, N.C., is used to calibrate the flow sensor 17 of the apparatus 10 to insure that each cigarette is submitted to the desired conditions.

The flow sensor 17 preferably includes an elongate tube-like body portion 30 of die-cast low density polyethylene construction. A typical sensor 17 is a tube, about 32 mm in length having an outside diameter of about 8 mm and an inner diameter of about 6 mm. A flow restrictor 31 of low density polyethylene is positioned in the central (i.e. hollow) portion of the body portion 30. Preferably, the flow restrictor 31 is generally cone-shaped or wide-mouthed at the cigarette end and includes a 2 mm passageway therethrough. The flow restrictor 31 is located between a pair of pressure taps 33, 34 and provides a pressure differential therebetween. Representative pressure taps 33, 34 are openings about 1 mm in diameter and are positioned about 10 to about 12 mm apart through the longitudinal periphery of the flow sensor 17.

In a preferred embodiment, the flow sensor 17 is connected via flexible plastic tubing 35 to a transducer system 37 comprising a series of transducers 39, 40, 41 which measures the pressure differential across the flow sensor 17. An exemplary transducer system 37 are three Model DP15-26 transducers manufactured by Validyne Engineering Corporation of Northridge, Calif. connected in series. Specifically, one transducer 39 measures pressure differential across one tap 33, while a second transducer 40 measures absolute pressure across the other tap 34, and a third transducer 41 is used to reduce noise transmitted by transducers 39, 40 in the sensor 17. The transducer system 37 is linked via wires 43, 44 to a demodulator 45 for signal amplification and demodulation. An exemplary demodulator 45 is Model MC1-3 also manufactured by Validyne Engineering Corporation. The data from the transducer/demodulator system are collected by a computer 47 such as an IBM Model AT computer manufactured by IBM of Armock, N.Y. connected to the demodulator 45 by wires 48 and a connecting board 49 such as Model 707 manufactured by Data Translation of Marlboro, Mass.

The transducer system 37 conveniently is calibrated for transducers 39, 40, 41 by measuring the voltage output of the transducers under a nominal vacuum of about 200 mm $H_2O$ and establishing a linear response range. All the transducers 39, 40, 41 are adjusted such that ambient pressure produces $0.0 \pm 0.02$ volts at transducer 39, and such that a 200 mm $H_2O$ vacuum produces a 10 volt output at transducer 40.

The flow sensor 17 is calibrated using the flow meter 29 and measuring the voltage output using a voltmeter (not shown) such as Model Micronta 22-185 Digital Multimeter manufactured by Radio Shack of Fort Worth, Tex. A flow rate is induced, ranging from 5 to 50 ml/sec, across 3 multicapillary calibration rods (not shown, but inserted for cigarette 15) known to cause pressure drops. For example, calibration rods providing pressure drops of about 114, 154, and 202 mm $H_2O$ respectively may be used. Exemplary calibration rods are available from Tennessee Eastman Co. of Kingsport, Tenn. The calibration rods are used to simulate pressure drops and the voltage responses are measured. A linear regression analysis of the voltage responses and induced flow rates is performed in order to determine the flow rate through a burning cigarette.

Figure 2:
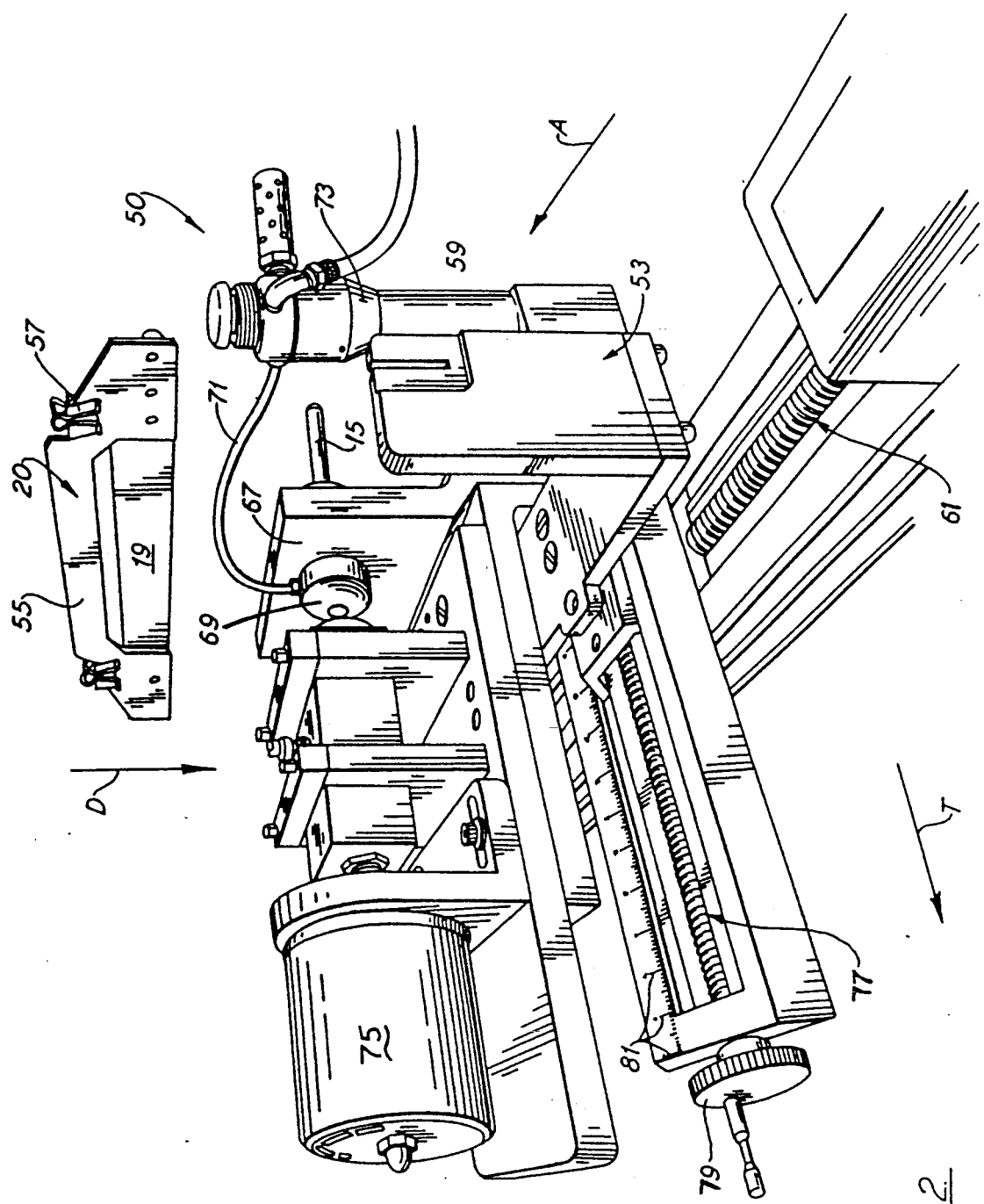
FIG. 2 is a perspective view of a preferred apparatus of the present invention and illustrates a portion of the apparatus shown in FIG. 1.

With reference to FIG. 2, a collection assembly 50 for collecting a discrete sample amount of smoke components from the drawn smoke is shown. The collection assembly 50 includes a filter pad 19 and a movable stage 53. The filter pad 19 is preferably a Cambridge filter pad (Cambridge Filter Corporation of Syracuse, N.Y.) and is characterized by its high efficiency of particulate removal (greater than 99% for particulates larger than 0.3 micron under FTC standard conditions). The filter pad 19 is typically a 15 cm by 2.5 cm rectangular pad.

The filter pad 19 is carried by a mount 20 or other suitable mounting means for securing the filter pad 19 and for allowing removal of the filter pad 19 after each successive individual puff. In a preferred embodiment, the mount 20 may include a metal or other resilient body 55 wherein the filter pad 19 is held in place using clips 57 or other fastening means. The filter pad 19 and the mount 20 are removably positioned on movable stage 53 or other suitable means for providing relative movement in direction of arrow T between the filter 19 and the path of travel of the drawn smoke in direction of arrow A. The filter pad 19 and mount 20 are shown in FIG. 2 as being removed from stage 53. Prior to the initiation of a puff, the filter pad 19 and mount 20 are moved downward in direction of arrow D and positioned in groove $9 within the stage 53. Preferably, the filter pad 19 is positioned a minimum distance away from the cigarette so that a minimal dead volume, as determined by the flow sensor 17 (not shown in FIG. 2), exists between the filter pad 19 and the cigarette 15.

In a preferred embodiment, the stage 53 is used to move the filter pad 19 in a controlled translational manner in direction of arrow T relative to the path of travel of the drawn smoke. This is preferably accomplished by positioning the stage 53 on a rotatable threaded rod 61 whose speed of rotation may be controlled by a control box 63 (see FIG. 1) attached to a motor (not shown). A suitable control box 63 is a Model E-552-M, manufactured by Electro-Craft Corp. of Hopkins, Minn. and a suitable motor is a Model B25212K1J motor manufactured by Unislide Velmex, Inc., of Holcomb, N.Y. Other control systems and motors will be apparent to those skilled in the art.

The stage 53 also includes a holder 67 for the cigarette 15. The holder 67 includes a mount 69 having a latex diaphragm (not shown) within the mount 69. A representative diaphragm is Part No. 20416-025 manufactured by American Hospital Supply of McGraw Park, Ill. The diaphragm is linked via Tygon ® tubing 71 to a slight vacuum source 73 which provides positive and negative pressure to the mount 69. A solenoid 7$ is mounted on the stage 53 and controls pressure experienced by the holder 67 and the mount 69 from the vacuum source. A suitable solenoid 75 is a Model S115 solenoid manufactured by Alco Valve Co. of St. Louis, Mo. Additionally, the distance between the cigarette 15 and the filter pad 19 may be adjusted using rotatable threaded rod 77. The threaded rod 77 may be rotated manually using a crank 79 as shown or by any other means to move the holder 67 relative to the filter pad 19. Other means for adjusting the distance between the holder 67 and filter pad 19 will be readily apparent to the skilled artisan. Additionally, indicia 81 on the stage 53 may be included to indicate the position of the stage 53 relative to the filter pad 19 and the mount 20.

In operation, the smoking machine 12 is adjusted to the desired FTC conditions and the cigarette 15 is lit. A puff is initiated by activating the enclosure 27. During this period of a puff, the filter pad 19 is moved preferably transversely to the path of the drawn smoke in order to collect discrete sample amounts of uniform distribution. For example, samples can be collected at 0.0 to 0.4, 0.4 to 0.8, 0.8 to 1.2, 1.2 to 1.6, and 1.6 to 2.0 second time segments during a two second puff. After each puff, during the smolder period, the filter pad 19 and the mount 20 are removed from the stage 53. A new filter pad 19 is inserted in the mount 20 and repositioned to collect a discrete sample from the next puff of the cigarette 15. A separate filter pad 19 is used for each successive puff of the cigarette. After the cigarette 15 has been completely smoked, it is removed and a new cigarette is mounted in the holder 67. The original or first filter pad 19 is then repositioned to collect a sample of smoke particulates. This repeated process allows replicate data collection. Preferably, the flow sensor 17 is removed after the first cigarette is smoked to reduce the dead volume between the filter pad 19 and the cigarette 15.

After a predetermined number of cigarettes 15 have been smoked each filter pad 19 is analyzed to determine the smoke components deposited on each segment. For example, gas chromatographs, scintillation counters and other means for determining the composition of smoke components may be used.

Thus it is readily apparent that the apparatus 10 of the present invention provides a means for collecting smoke components of drawn smoke during a predetermined time interval within each individual puff. The apparatus 10 provides relative movement between the filter pad 19 and the path of travel of the drawn smoke to enable the collection of discrete sample amounts of uniform distribution on sequential segments of the filter pad 19.

In the Figures and specification, there have been disclosed preferred embodiments of the invention. While specific terms are employed, they are used in a generic and descriptive sense only, and not for the purpose of limiting the scope of the invention being set forth in the following claims.

That which is claimed is:

1. An apparatus for collecting components of mainstream smoke of a smoking article, said apparatus comprising
    a) means for drawing successive individual puffs of smoke from the smoking article,
    b) means for providing a predetermined path of travel for smoke drawn from the smoking article, and
    c) means for collecting a discrete sample amount of smoke components from the drawn smoke during a predetermined time interval within each individual puff, said collection means including:
        (i) filter means positioned within the predetermined path of the drawn smoke for collecting smoke components therefrom, and
        (ii) means for providing relative movement between said filter means and said path of travel of the drawn smoke to collect discrete sample amounts of substantially uniform distribution on different portions of the filter means from predetermined spaced apart segments of the drawn smoke during the predetermined time interval.

2. An apparatus according to claim 1 wherein said means for providing relative movement between said filter means and said path of travel of the drawn smoke causes transverse movement of said filter means relative to said path of travel of the drawn smoke.

3. An apparatus according to claim 1 wherein said means for collecting includes means mounting said filter means allowing removal thereof after each successive individual puff.

4. An apparatus according to claim 1 wherein said means for drawing successive individual puffs of smoke from the smoking article includes means for initiating successive individual puffs.

5. An apparatus for collecting components of mainstream smoke of a smoking article, said apparatus comprising
    a) means for drawing successive individual puffs of smoke from the smoking article,
    b) means for providing a predetermined path of travel for smoke drawn from the smoking article, and
    c) means for collecting a discrete sample amount of smoke components from the drawn smoke during a predetermined time interval within each individual puff, said collection means including:
(i) filter means positioned within the predetermined path of the drawn smoke for collecting smoke components therefrom, and
(ii) means for providing relative transverse movement between said filter means and said path of travel of the drawn smoke to collect discrete sample amounts on different portions of the filter means from predetermined spaced apart segments of the drawn smoke during the predetermined time interval.

6. An apparatus according to claim 5 wherein means for providing relative transverse movement between said filter means and said path of travel of the drawn smoke causes transverse movement of said filter means relative to said path of travel of the drawn smoke.

7. An apparatus according to claim 6 wherein said means for drawing successive individual puffs of smoke from the smoking article comprises means for initiating successive individual puffs.

8. An apparatus for collecting components of mainstream smoke of a smoking article, said apparatus comprising
a) means for drawing successive individual puffs of smoke from the smoking article,
b) means for providing a predetermined path of travel for smoke drawn from the smoking article, and
c) means for collecting a discrete sample amount of smoke components from drawn smoke during a predetermined time interval within each individual puff, said collection means including:
(i) filter means positioned within the predetermined path of the drawn smoke for collecting smoke components from the drawn smoke,
(ii) movable storage means for moving said filter means transversely relative to the path of travel of the drawn smoke to collect discrete sample amounts on different portions of the filter means from predetermined spaced apart segments of the drawn smoke during the predetermined time interval, and
(iii) means for mounting said filter means on said stage means and for allowing removal of the filter means from said stage means after each successive individual puff.

9. An apparatus according to claim 8 wherein said means for drawing successive individual puffs of smoke from the smoking article includes means for initiating successive individual puffs.

10. A method for collecting components of mainstream smoke of a smoking article, said method comprising the steps of:
(a) drawing an individual puff of smoke from the smoking article along a predetermined path of travel, and
(b) transversely moving a filter means linearly relative to the path of travel of the drawn smoke to collect discrete sample amounts of smoke components from the drawn smoke on different portions of the filter means from predetermined spaced apart segments of the drawn smoke during the predetermined time interval.

11. A method for collecting components of mainstream smoke from successive individual puffs of a smoking article said method comprising the steps of:
(a) drawing a first individual puff of smoke from the smoking article along a predetermined path of travel;
(b) transversely moving a first filter means relative to the path of travel of drawn smoke to collect discrete sample amounts of smoke components from the drawn smoke on different portions of the filter means from predetermined spaced apart segments of the drawn smoke during the predetermined time interval;
(c) removing said first filter means and inserting a second filter means; and
(d) repeating steps (a)-(c) until the smoking article is substantially completely smoked.

* * * * *